(12) United States Patent
Nelson

(10) Patent No.: US 10,159,588 B1
(45) Date of Patent: *Dec. 25, 2018

(54) SELF ADJUSTING KNEE BRACE

(71) Applicant: Mueller Sports Medicine, Inc., Prairie du Sac, WI (US)

(72) Inventor: Ronald E. Nelson, Cambridge, WI (US)

(73) Assignee: Mueller Sports Medicine, Inc., Prairie du Sac, WI (US)

( * ) Notice: Subject to any disclaimer, the term of this patent is extended or adjusted under 35 U.S.C. 154(b) by 347 days.

This patent is subject to a terminal disclaimer.

(21) Appl. No.: 15/005,552

(22) Filed: Jan. 25, 2016

Related U.S. Application Data

(63) Continuation of application No. 10/379,208, filed on Mar. 4, 2003, now Pat. No. 9,314,364.

(51) Int. Cl.
*A61F 5/01* (2006.01)

(52) U.S. Cl.
CPC .......... *A61F 5/0106* (2013.01); *A61F 5/0109* (2013.01)

(58) Field of Classification Search
CPC .. A61F 5/00; A61F 5/01; A61F 5/0102; A61F 5/0106; A61F 5/0109; A61F 5/0123; A61F 5/37; A61F 13/06; A61F 13/061; A61H 1/00; A61H 1/02; A61H 1/0237; A61H 1/024
USPC ........ 602/5, 16, 23, 26, 60–63, 75; 128/846, 128/869–870, 882
See application file for complete search history.

(56) References Cited

U.S. PATENT DOCUMENTS

| | | | |
|---|---|---|---|
| 1,092,836 | A | 4/1914 | Hart |
| 1,622,211 | A | 3/1927 | Sheehan |
| 2,729,821 | A | 1/1956 | Freudenberg |
| 3,046,981 | A | 7/1962 | Biggs, Jr. |
| 3,710,397 | A | 1/1973 | Tsujimoto |
| 3,902,482 | A | 9/1975 | Taylor |
| 3,934,583 | A | 1/1976 | Hollingshead |
| 3,935,858 | A | 2/1976 | Harroff |
| 4,084,586 | A | 4/1978 | Hettick |
| 4,296,744 | A | 10/1981 | Palumbo |
| 4,334,528 | A | 6/1982 | Gauvry |
| 4,366,813 | A | 1/1983 | Nelson |
| 4,379,463 | A | 4/1983 | Meier |
| 4,573,455 | A | 3/1986 | Hoy |
| 4,651,722 | A | 3/1987 | Karczewski |

(Continued)

*Primary Examiner* — Tarla R Patel
(74) *Attorney, Agent, or Firm* — Rick L. Abegglen

(57) ABSTRACT

A knee brace for use by athletes or others requiring protection and support of the knee. The knee brace protects against abnormal motions of the knee, and provides direct and indirect patella stabilization. A base comprised of elastic material is configured to closely fit around portions of the knee and adjacent leg portions. Direct patella support is provided by upper crossed straps that are permanently fastened to the base and cross the front of the leg above the knee, or by lower crossed straps that are permanently fastened to the base and cross the front of the leg below the knee, or by both upper and lower crossed straps. Additional direct patella support may be provided by a patella opening. One or more generally upright lateral pockets containing semi-rigid stays may also be provided on the sides of the base for lateral support. A popliteal opening may be provided to reduce the possibility of chafing at the rear of the knee.

46 Claims, 5 Drawing Sheets

(56) References Cited

U.S. PATENT DOCUMENTS

| | | |
|---|---|---|
| 4,686,969 A | 8/1987 | Scott |
| 4,726,362 A | 2/1988 | Nelson |
| 4,805,606 A | 2/1989 | McDavid, III |
| 4,844,057 A | 7/1989 | Hoy |
| 5,016,621 A | 5/1991 | Bender |
| 5,085,210 A | 2/1992 | Smith, III |
| 5,086,761 A | 2/1992 | Ingram |
| 5,154,690 A | 10/1992 | Shiono |
| 5,221,252 A | 6/1993 | Caprio, Jr. |
| 5,261,871 A | 11/1993 | Greenfield |
| 5,267,951 A | 12/1993 | Ishii |
| 5,297,296 A | 3/1994 | Moretz |
| 5,316,546 A | 5/1994 | Lindh |
| 5,399,153 A | 5/1995 | Caprio, Jr. |
| 5,411,037 A | 5/1995 | Hess |
| 5,417,646 A | 5/1995 | Gauvry |
| 5,512,039 A | 4/1996 | White |
| 5,513,658 A | 5/1996 | Goseki |
| 5,514,082 A | 5/1996 | Smith, III |
| 5,514,083 A | 5/1996 | Smith, III |
| 5,562,605 A | 10/1996 | Taylor |
| 5,613,943 A | 3/1997 | Palumbo |
| 5,626,557 A | 5/1997 | Mann |
| 5,656,023 A | 8/1997 | Caprio, Jr. |
| 5,711,312 A | 1/1998 | Staudinger |
| 5,728,057 A | 3/1998 | Ouellette |
| 5,728,058 A | 3/1998 | Ouellette |
| 5,730,710 A | 3/1998 | Eichhorn |
| 5,759,167 A | 6/1998 | Shields, Jr. |
| 5,792,084 A | 8/1998 | Wilson |
| 5,797,864 A | 8/1998 | Taylor |
| 5,807,298 A | 9/1998 | Palumbo |
| 5,823,981 A | 10/1998 | Grim |
| 5,865,776 A | 2/1999 | Springs |
| 5,865,777 A | 2/1999 | Detty |
| 5,865,782 A | 2/1999 | Fareed |
| 5,873,848 A | 2/1999 | Fulkerson |
| 5,925,010 A | 7/1999 | Caprio, Jr. |
| 5,944,682 A | 8/1999 | Milana-Panopoulis |
| 6,063,048 A | 5/2000 | Bodenschatz |
| 6,077,242 A | 6/2000 | Falk |
| 6,080,124 A | 6/2000 | Falk |
| 6,110,135 A | 8/2000 | Madow |
| 6,142,965 A | 11/2000 | Mathewson |
| 6,156,001 A | 12/2000 | Frangi |
| 6,311,337 B1 | 11/2001 | Tollini |
| 6,402,712 B1 | 6/2002 | Gauvry |
| 6,436,066 B1 | 8/2002 | Lockhart |
| 6,551,264 B1 | 4/2003 | Cawley |
| 6,773,411 B1 | 8/2004 | Alvarez |
| 9,314,364 B2 * | 4/2016 | Nelson .................. A61F 5/0106 |
| 2003/0176826 A1 | 9/2003 | Scott |
| 2003/0187375 A1 | 10/2003 | Gaylord |

* cited by examiner

SELF ADJUSTING KNEE BRACE

CROSS REFERENCE TO RELATED APPLICATIONS

This application claims priority to application Ser. No. 10/379,208 filed Mar. 4, 2003, the disclosure of which is incorporated herein by reference in its entirety for continuity of disclosure.

FIELD OF THE INVENTION

This invention relates generally to the field of articles worn by persons to reduce the likelihood, severity, or exacerbation of injury to the body, and more specifically to the field of braces worn on the knee.

BACKGROUND OF THE INVENTION

Flexible knee braces are used by athletes and other persons engaged in vigorous physical activity to protect the knee from injury and to avoid exacerbation of existing injury. The knee is one of the most heavily used joints of the body, as it is used in any activity that involves walking or running. The knee is also a common subject of injury, due to the relatively high levels of stress it must bear. During normal ambulation, in occupations involving physical labor, and especially during strenuous sports, the knee can undergo abnormal motions as a result of quick changes in direction, fatigue, uneven surfaces, or impacts. These abnormal motions can cause sprains or more serious injuries, including dislocation, stretching, or tearing of the tissues that make up the knee.

Several different types of abnormal motion can cause injury to the knee. First, hyperextension of the knee joint can occur, wherein the knee flexes in its normal front to back fashion but beyond its normal range of motion. A second type of abnormal motion is axial rotation, wherein the lower leg is twisted rotationally relative to the thigh about the knee joint. A third type of abnormal motion is lateral flexure of the lower leg relative to the thigh, wherein the knee joint flexes from side to side instead of the normal front to back motion. In addition, abnormal motion of the patella (kneecap) can result in injuries such as chondromalacia patella, which is a softening or degeneration of the undersurface of the patella, and dislocation of the patella, also known as subluxation of the patella.

Devices to protect the knee against abnormal motions have been used for many years, in a variety of specific embodiments which vary in their abilities to protect against the different types of abnormal motions. Besides protecting the knee against abnormal motions, the devices sometimes provide additional benefits such as insulating the knee to keep it warm, protecting the knee against impact, or compressing the knee to reduce discomfort. However, the protections afforded by these devices against abnormal motion are often accompanied by a reduction in range or ease of normal motion. These devices can also have other undesirable aspects such as added weight on the leg, potential for self-injury or injury to others caused by rigid components, difficulty of application and removal, cost, appearance, and irritation or chafing of the skin.

For these reasons, there has long been motivation to find an improved knee brace which can protect the knee from abnormal motions without affecting the range or ease of normal motion, while avoiding the undesirable aspects of prior art devices.

SUMMARY OF THE INVENTION

A knee brace according to the present invention includes crossed support straps which are permanently fixed to the base of the brace. This eliminates any need to fasten the crossed support straps, thereby avoiding the possibility of error during application of the brace, and helps to ensure the proper fit at all times of the crossed support straps. Further, as the knee moves between flexion and extension positions, the straps self-adjust to the position of the knee.

A knee brace according to the invention preferably includes both upper and lower crossed support straps, but this is not necessary. A knee brace according to the invention may include upper crossed straps without lower crossed support straps, or such a knee brace may include lower crossed straps without upper crossed support straps. The midpoints of the crossed straps may be fastened to each other, or to the base, although this is not required.

According to another aspect of the invention, the knee brace may include one or more upright support members fastened to either or both sides of the base, although this is not required. The upright support members may be a resilient stay member, or a hinge, or other upright support members known in the art. The upright support member may be removable.

According to another aspect of the invention, the knee brace may include a diamond shaped or round opening around the patella (kneecap), although other shapes could be used. A preferred embodiment includes a diamond-shaped opening which may conform to the shape of the patella particularly well.

According to another aspect of the invention, the knee brace may include a circular opening over the popliteal area (the area at the rear of the knee). Such a popliteal opening can decrease the chance of irritation of the skin in that area.

A knee brace according to the invention can protect against all forms of abnormal knee motion and provide patella support, while avoiding undue restriction of movement or bunching. It can provide therapeutic warming without undue moisture buildup. It is easy to adjust, fasten, and remove, and it can be used by a wide range of people with a variety of knee problems and knee sizes.

Further objects, features, and advantages of the invention will be apparent from the following detailed description when taken in conjunction with the accompanying drawings.

DETAILED DESCRIPTION OF THE INVENTION

Figure 1:
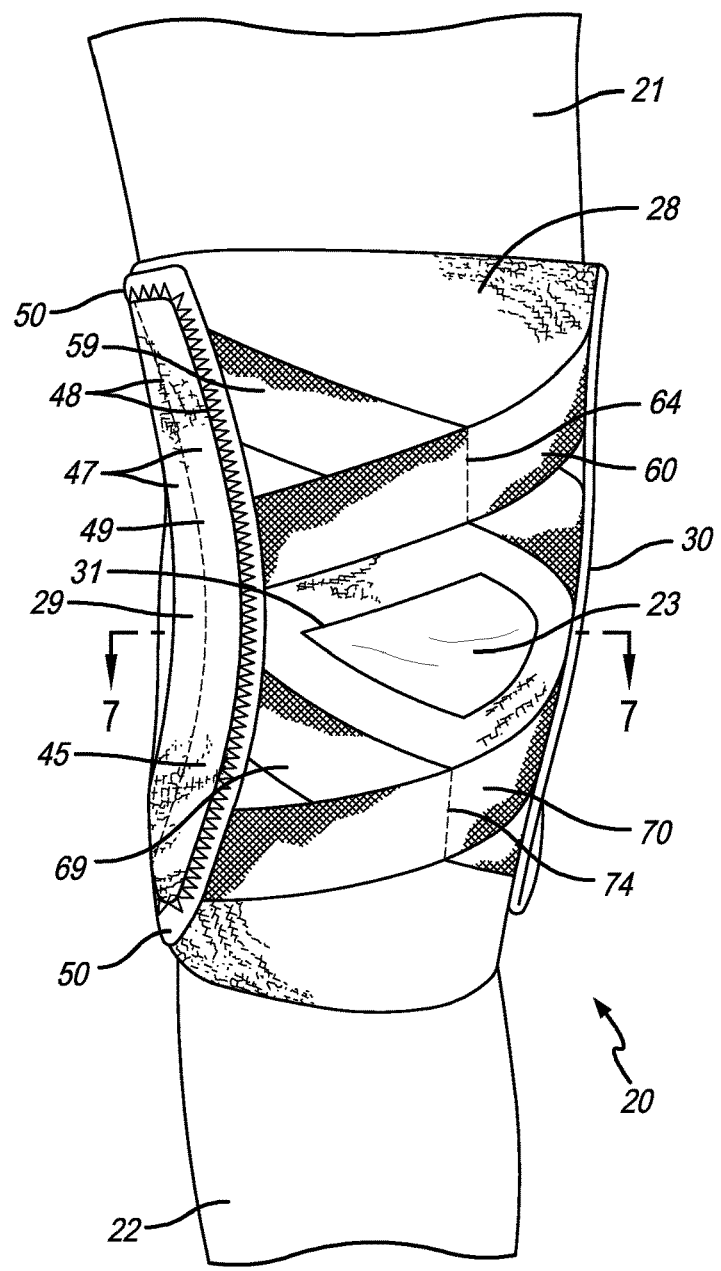
FIG. 1 is a front perspective view of a knee brace according to the invention fitted on the leg of a person.

Referring to the drawings, FIGS. 1-4 show a preferred embodiment of a knee brace according to the invention indicated generally at 20. As normally worn by a person, the upper leg 21 extends from an opening at the top of the knee brace 20, and the lower leg 22 extends from an opening at the bottom of the knee brace 20.

The knee brace 20 includes a base 28, having a first side 29 and a second side 30, which is preferably formed as a reclosable sleeve made from a sheet of elastic material which provides generalized support and compression to the knee area, along with therapeutic warming, but other materials may be used. The base 28 may also be formed, for example, of a tubular elastic sleeve shaped to fit snugly about the knee and adjacent leg portions.

The base 28 may include a patella opening 31 which generally matches the size of the patella, such that the patella (kneecap) 23 of the wearer extends from the patella opening 31 when the brace 20 is worn, although this is not necessary. The patella opening 31 is preferably diamond-shaped, but this is not necessary and other shapes may be used. In addition to providing direct patella stabilization, the patella opening 31 may help to locate the brace 20 with respect to the patella 23 during application of the brace 20.

Figure 3:
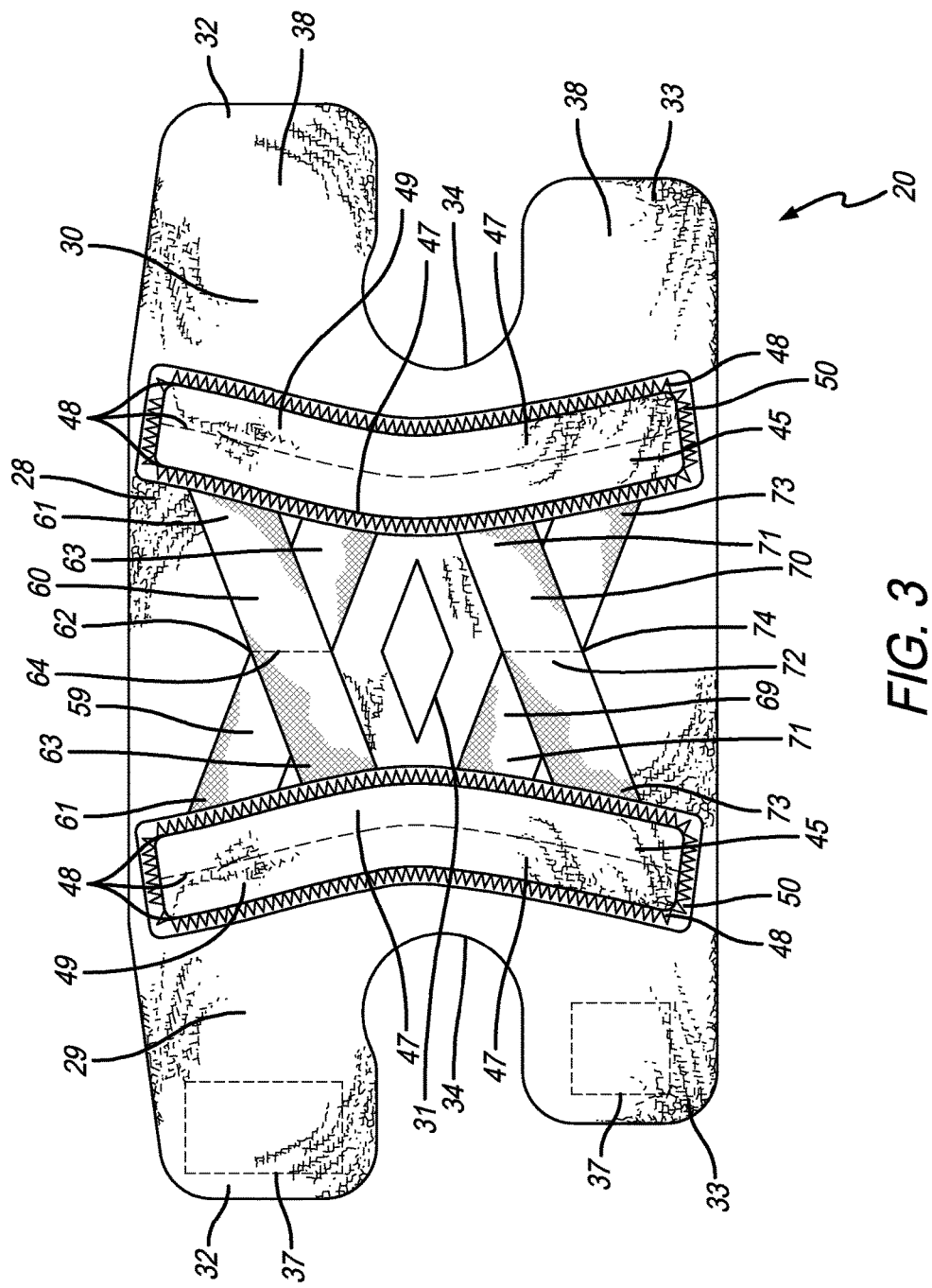
FIG. 3 is a front view of a knee brace according to the invention laid flat.
Figure 4:
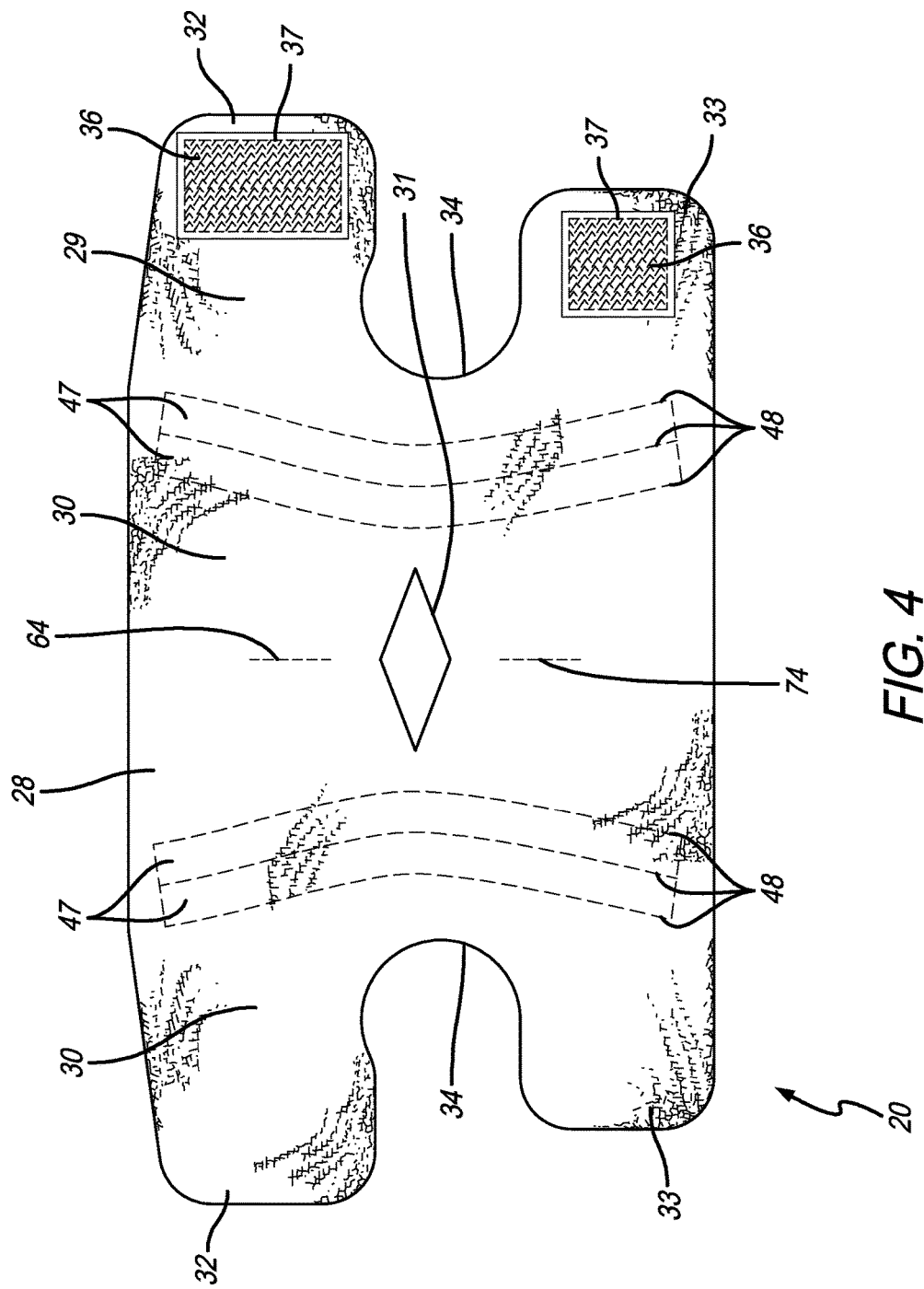
FIG. 4 is a rear view of a knee brace according to the invention laid flat.

As best shown in FIGS. 3 and 4, the first side 29 and second side 30 of the base 28 are preferably each formed to terminate in upper fastening tabs 32 and lower fastening tabs 33. When the base 28 of the knee brace 20 is wrapped about the leg of a person, the pair of upper fastening tabs 32 overlap at the rear of the leg where they may be detachably attached together in order to fasten the knee brace 20 about the upper leg 21 of the wearer. Similarly, the pair of lower fastening tabs 33 overlap at the rear of the leg where they may be detachably attached together in order to fasten the knee brace 20 about the lower leg 22 of the wearer.

A gap 34 may be provided between the upper fastening tabs 32 and the lower fastening tabs 33, so that when the knee brace 20 is fitted upon the leg the gaps on each side form a popliteal opening 35 at the rear of the knee, to avoid chafing, provide ventilation, and avoid bunching or undue restriction of movement, although this is not required.

In a preferred embodiment, each pair of upper fastening tabs 32 and lower fastening tabs 33 may be detachably attached together, preferably using hook and loop material of the type which adheres when pressed together. Areas of hook type fastening material 36 may be fastened, for example by stitches 37, onto one of the upper fastening tabs 32 and one of lower fastening tabs 33. The other upper fastening tab 32 and the other lower fastening tab 33 (which do not bear areas of hook type fastening material 36) may be partially or entirely covered in loop type fastener material 38.

When the base 28 of the knee brace 20 is wrapped about the leg with the areas of hook type fastening material 36 on one upper fastening tab 32 and one lower fastening tab 33 overlapping and engaging the loop type fastening material 38 on the other upper fastening tab 32 and the other lower fastening tab 33, each pair of upper fastening tabs 32 and lower fastening tabs 33 may be detachably attached by pressing them together, thereby fastening the brace about the leg of the wearer.

Figure 2:
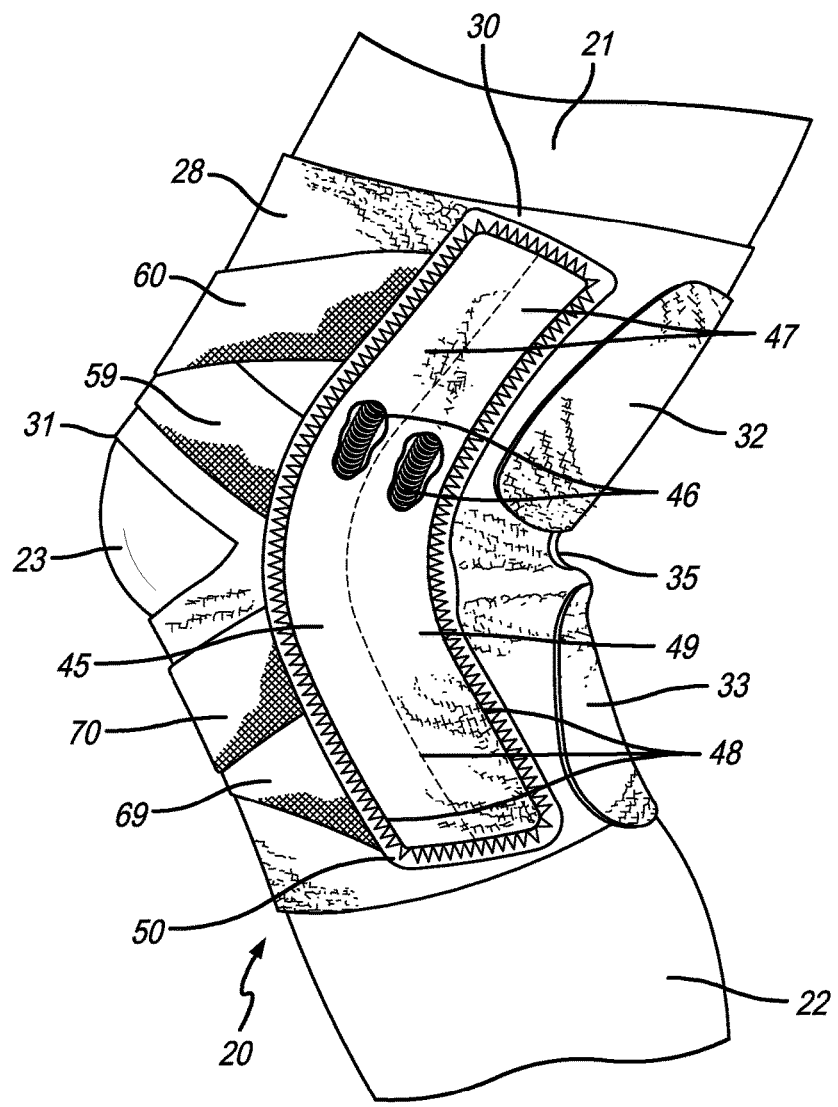
FIG. 2 is a side view of a knee brace according to the invention fitted on the leg of a person.
Figure 5:
FIG. 5 is a side view of an exemplary resilient stay member.
Figure 6:
FIG. 6 is a front view of an exemplary resilient stay member.
Figure 7:
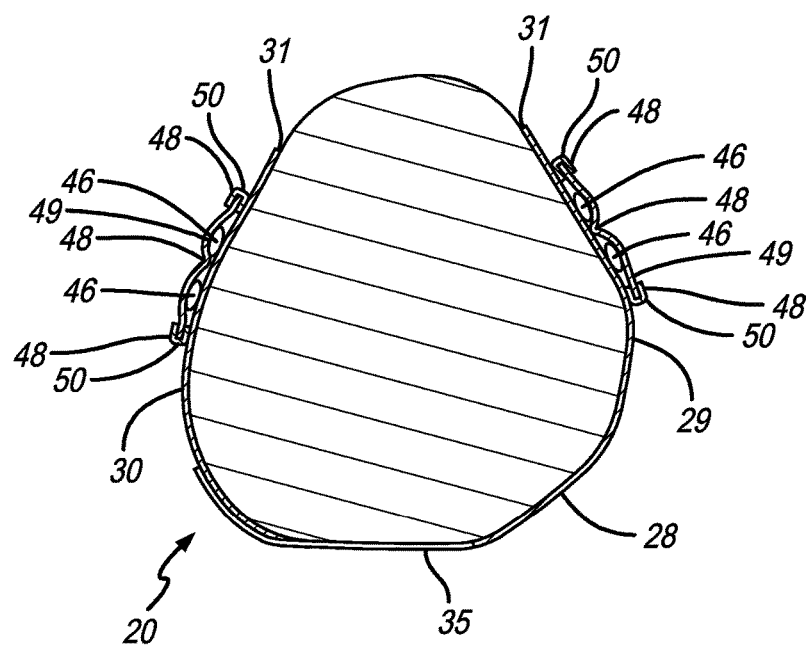
FIG. 7 is a cross-sectional view of the knee brace of FIG. 1 taken along the line 7-7 thereof.

As shown in FIG. 2 and as shown in cross-section in FIG. 7, one or more upright support members 45 may be provided on the first side 29 or second side 30 or on both sides of the base of the knee brace, to provide support and protect the knee against abnormal motions, although this is not required. In a preferred embodiment, the upright support members 45 may be formed, for example, by placing a resilient stay member 46 in an elongated side pocket 47. As shown in FIGS. 5 and 6, the resilient stay members 46 are preferably comprised of a flattened spiral core of stainless steel or other flexible material of conventional construction commonly used in various types of braces.

The elongate side pocket 47 may be formed, for example, between vertical sewn seams 48 that fix a side pocket cover strip 49 to the base 28. The side pocket cover strip 49 may be made of the same elastic sheet material as the base 28 of the knee brace 20, although this is not necessary. Edge binding 50 may be fastened to the edges of the side pocket cover strips 49, for example using stitches 48, although this is not necessary.

As shown in FIGS. 1-4, a preferred embodiment of a knee brace according to the invention includes a first upper support strap 59 and a second upper support strap 60, each upper support strap having an upper end 61, a midpoint 62, and a lower end 63. The first upper support strap 59 and second upper support strap 60 are permanently fastened to the base 28 in a crossed fashion, by permanently fastening the upper end 61 of the first upper support strap 59 and the lower end 63 of the second upper support strap 60 to the first side 29 of the base and by permanently fastening the upper end 61 of the second upper support strap 60 and the lower end 63 of the first upper support strap 59 to the second side 30 of the base, preferably using the stitches 48 which secure the side pocket cover strips 49 to the base 28. The midpoints 62 of the crossed first upper support strap 59 and second upper support strap 60 may also be permanently fastened together, or fastened to the base, preferably using stitches 64.

As shown in FIGS. 1-4, a preferred embodiment of a knee brace according to the invention may also include a first lower support strap 69 and a second lower support strap 70, each lower support strap having an upper end 71, a midpoint 72, and a lower end 73. The first lower support strap 69 and second lower support strap 70 are preferably permanently fastened to the base 28 in a crossed fashion, by permanently fastening the upper end 71 of the first lower support strap 69 and the lower end 73 of the second lower support strap 70 to the first side 29 of the base and by permanently fastening the upper end 71 of the second lower support strap 70 and the lower end 73 of the first lower support strap 69 to the second side 30 of the base, preferably using the stitches 48 which secure the side pocket cover strips 49 to the base 28. The midpoints 72 of the crossed first lower support strap 69 and second lower support strap 70 may also be permanently fastened together, or fastened to the base 28, preferably using stitches 74.

There are various possibilities with regard to alternative embodiments of a knee brace according to the invention.

Although in a preferred embodiment the knee brace 20 includes a base 28 which is formed as a reclosable sleeve made from a sheet of elastic material, this is not required. For example, the base 28 may also be formed of a tubular elastic sleeve shaped to fit snugly about the knee and adjacent leg portions. The base 28 does not need to include a patella opening 31, and the patella opening 31, if present, could have a variety of shapes, e.g. circular, square, rectangular, elliptical, diamond, trapezoidal, or any substantial equivalent. All such alternative embodiments will be referred to herein as a base.

Although in a preferred embodiment the first side 29 and second side 30 of the base each terminate in upper fastening tabs 32 and lower fastening tabs 33, with a side gap 34 between the upper and lower fastening tabs, this is not required. For example, the first side 29, or the second side 30, or both sides of the base, or portions thereof, could be straight.

Although in a preferred embodiment the base is detachably fastened about the leg of the wearer using hook and loop material of the type which adheres when pressed together, this is not required. For example, other fasteners such as buttons, clasps, buckles, pins, zippers, straps, buttons or other substantial equivalents may be substituted for the hook and loop type fastener material.

Although in a preferred embodiment, various components are permanently fastened together using stitches, this is not required. For example, other means such as glue, thermal bonding, or other substantial equivalents could be used.

Although in a preferred embodiment, two upright support members 45 (shown in cross-section in FIG. 7) are provided on the first side 29 and second side 30 of the base of the knee brace, this is not necessary, and the exact number, location, and construction of the upright support members 45 may vary. For example, there may be a single elongated side pocket 47 forming only one upright support member 45, or there may be one or more elongated side pockets 47 on each side of the knee with a resilient stay 46 in each elongated side pocket 47. The elongated side pockets 47 may be openable at one end to allow removal of the resilient stays 46, so that the brace may be washed or so that different resilient stays 46 may be inserted to adjust the amount and type of support provided. The upright support members 45 may include mechanical hinges, plastic rods, metal rods, narrow strips of reinforcing sheet material, or other substantial equivalents, or a combination of these various alternatives.

As shown in FIGS. 1-4, a preferred embodiment of a knee brace according to the invention may include crossed first upper support strap 59 and second upper support strap 60 and crossed first lower support strap 69 and second lower support strap 70, wherein the ends of each pair of crossed support straps are permanently fastened to the base, although other arrangements are possible. For example, there may be a pair of crossed upper support straps which are permanently fastened to the base, without a pair of crossed lower support straps which are permanently fastened to the base, or with lower support straps arranged in a different configuration. Similarly, there may be a pair of crossed lower support straps which are permanently fastened to the base, without a pair of crossed upper support straps which are permanently fastened to the base, or with upper support straps arranged in a different configuration.

It is understood that the invention is not confined to the embodiments set forth herein as illustrative, but embraces all such forms thereof that come within the scope of the following claims.

What is claimed is:

1. A knee brace, comprising:
   (a) a base wearable in snug covering relationship to portions of a knee and adjacent portions of a leg of a person, the base having a first side and a second side;
   (b) a first upper support strap having an upper end, a midpoint, and a lower end, with the upper end of the first upper support strap permanently fastened to the first side of the base above the knee and the lower end of the first upper support strap permanently fastened to the second side of the base above the knee; and
   (c) a second upper support strap having an upper end, a midpoint, and a lower end, with the upper end of the second upper support strap permanently fastened to the second side of the base above the knee and the lower end of the second upper support strap permanently fastened to the first side of the base above the knee;
   wherein the first upper support strap and the second upper support strap are permanently fastened to the base in a crossed fashion;
   whereby the upper support straps self-adjust to the position of the knee as the knee moves between flexion and extension.

2. The knee brace of claim 1 wherein the midpoint of the first upper support strap and the midpoint of the second upper support strap are permanently fastened together.

3. The knee brace of claim 1 wherein the midpoint of the first upper support strap and the midpoint of the second upper support strap are permanently fastened to the base.

4. The knee brace of claim 1 wherein the base is a tubular sleeve.

5. The knee brace of claim 1 wherein the base is an openable and reclosable sleeve.

6. The knee brace of claim 1 wherein the base includes an patella opening.

7. The knee brace of claim 6 wherein the patella opening is diamond shaped.

8. The knee brace of claim 1 including at least one popliteal opening when the knee brace is worn.

9. The knee brace of claim 1 further comprising at least one upright support member fastened to a side of the base.

10. The knee brace of claim 9 wherein at least one upright support includes a resilient stay member.

11. The knee brace of claim 10 wherein the resilient stay member is removable.

12. The knee brace of claim 9 wherein the midpoint of the first upper support strap and the midpoint of the second upper support strap are permanently fastened together.

13. The knee brace of claim 9 wherein the midpoint of the first upper support strap and the midpoint of the second upper support strap are permanently fastened to the base.

14. The knee brace of claim 9 wherein the base includes an patella opening.

15. The knee brace of claim 14 wherein the patella opening is diamond shaped.

16. The knee brace of claim 9 including at least one popliteal opening when the knee brace is worn.

17. A knee brace, comprising:
   (a) a base wearable in snug covering relationship to portions of a knee and adjacent portions of a leg of a person, the base having a first side and a second side;
   (b) a first lower support strap having an upper end, a midpoint, and a lower end, with the upper end of the first lower support strap permanently fastened to the first side of the base below the knee and the lower end of the first lower support strap permanently fastened to the second side of the base below the knee; and
   (c) a second lower support strap having an upper end, a midpoint, and a lower end, with the upper end of the second lower support strap permanently fastened to the second side of the base below the knee and the lower end of the second lower support strap permanently fastened to the first side of the base below the knee;
   wherein the first lower support strap and the second lower support strap are permanently fastened to the base in a crossed fashion;
   whereby the lower support straps self-adjust to the position of the knee as the knee moves between flexion and extension.

18. The knee brace of claim 17 wherein the midpoint of the first lower support strap and the midpoint of the second lower support strap are permanently fastened together.

19. The knee brace of claim 17 wherein the midpoint of the first lower support strap and the midpoint of the second lower support strap are permanently fastened to the base.

20. The knee brace of claim 17 wherein the midpoint of the first lower support strap and the midpoint of the second lower support strap are permanently fastened together, and the midpoint of the first lower support strap and the midpoint of the second lower support strap are permanently fastened to the base.

21. The knee brace of claim 17 wherein the base is a tubular sleeve.

22. The knee brace of claim 17 wherein the base is an openable and reclosable sleeve.

23. The knee brace of claim 17 wherein the base includes an patella opening.

24. The knee brace of claim 23 wherein the patella opening is diamond shaped.

25. The knee brace of claim 17 including at least one popliteal opening when the knee brace is worn.

26. The knee brace of claim 17 further comprising at least one upright support member fastened to a side of the base.

27. The knee brace of claim 26 wherein at least one upright support includes a resilient stay member.

28. The knee brace of claim 27 wherein the resilient stay member is removable.

29. The knee brace of claim 26 wherein the midpoint of the first lower support strap and the midpoint of the second lower support strap are permanently fastened together.

30. The knee brace of claim 26 wherein the midpoint of the first lower support strap and the midpoint of the second lower support strap are permanently fastened to the base.

31. The knee brace of claim 26 wherein the base includes an patella opening.

32. The knee brace of claim 31 wherein the patella opening is diamond shaped.

33. The knee brace of claim 26 including at least one popliteal opening when the knee brace is worn.

34. A knee brace, comprising:
(a) a base wearable in snug covering relationship to portions of a knee and adjacent portions of a leg of a person, the base having a first side and a second side;
(b) a first upper support strap having an upper end, a midpoint, and a lower end, with the upper end of the first upper support strap permanently fastened to the first side of the base above the knee and the lower end of the first upper support strap permanently fastened to the second side of the base above the knee; and
(c) a second upper support strap having an upper end, a midpoint, and a lower end, with the upper end of the second upper support strap permanently fastened to the second side of the base above the knee and the lower end of the second upper support strap permanently fastened to the first side of the base above the knee;
(d) a first lower support strap having an upper end, a midpoint, and a lower end, with the upper end of the first lower support strap permanently fastened to the first side of the base below the knee and the lower end of the first lower support strap permanently fastened to the second side of the base below the knee; and
(e) a second lower support strap having an upper end, a midpoint, and a lower end, with the upper end of the second lower support strap permanently fastened to the second side of the base below the knee and the lower end of the second lower support strap permanently fastened to the first side of the base below the knee;
wherein the first upper support strap and the second upper support strap are permanently fastened to the base in a crossed fashion and the first lower support strap and the second lower support strap are permanently fastened to the base in a crossed fashion;
whereby the upper support straps and the lower support straps self-adjust to the position of the knee as the knee moves between flexion and extension.

35. The knee brace of claim 34 wherein the midpoint of the first upper support strap and the midpoint of the second upper support strap are permanently fastened together.

36. The knee brace of claim 34 wherein the midpoint of the first lower support strap and the midpoint of the second lower support strap are permanently fastened together.

37. The knee brace of claim 34 wherein the midpoint of the first upper support strap and the midpoint of the second upper support strap are permanently fastened together, and wherein the midpoint of the first lower support strap and the midpoint of the second lower support strap are permanently fastened together.

38. The knee brace of claim 34 wherein the midpoint of the first upper support strap and the midpoint of the second upper support strap are permanently fastened to the base.

39. The knee brace of claim 34 wherein the midpoint of the first lower support strap and the midpoint of the second lower support strap are permanently fastened to the base.

40. The knee brace of claim 34 wherein the base is a tubular sleeve.

41. The knee brace of claim 34 wherein the base is an openable and reclosable sleeve.

42. The knee brace of claim 34 wherein the patella opening is diamond shaped.

43. The knee brace of claim 34 including at least one popliteal opening when the knee brace is worn.

44. The knee brace of claim 34 further comprising at least one upright support member fastened to a side of the base.

45. The knee brace of claim 44 wherein at least one upright support includes a resilient stay member.

46. The knee brace of claim 45 wherein the resilient stay member is removable.

* * * * *